(12) United States Patent
Foerster et al.

(10) Patent No.: US 6,372,509 B1
(45) Date of Patent: Apr. 16, 2002

(54) SITU COPPER (I)

(75) Inventors: John W. Foerster, Millersville; Kenneth Ewing; Angela Ervin, both of Crofton; Robert Lamontagne, Bethesda, all of MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/040,331

(22) Filed: Mar. 18, 1998

(51) Int. Cl.⁷ .............................................. G01N 33/20
(52) U.S. Cl. ........................ 436/80; 436/73; 436/166; 436/169
(58) Field of Search ........................... 436/73, 80, 164, 436/166, 169

(56) References Cited

U.S. PATENT DOCUMENTS 3,748,096 A * 7/1973 Schmitt et al. ............. 436/80
4,793,977 A * 12/1988 Morris ....................... 422/55

FOREIGN PATENT DOCUMENTS

| JP | 6-249775 | * 9/1994 |
| JP | 7-63768 | * 3/1995 |

OTHER PUBLICATIONS

R. Tamilarasan et al, Inorg. Chem. 1988, 27, 4082–4084.*
K. Ohzeki et al, Analyst 1990, 115, 23–28.*
K. Yoshimura et al, Anal. Chim. Acta 1992, 268, 225–233.*
O. P. Shvoeva et al, J. Anal. Chem. 1997, 52, 76–80.*
L. B. Bjorklund et al, Anal. Chim. Acta 1997, 343, 259–266.*
R. Tandon et al, J. Membrane Sci. 1997, 136, 207–219.*
T. Takahashi et al, Chem. Abstr. 1973, 78, abstract 118813f.*
K. Yoshimura et al, Talanta 1976, 23, 449–454.*
M. Ohta et al, Bull. Chem. Soc. Jpn. 1984, 57, 3571–3573.*
H. Akaiwa et al, Chem. Abstr. 1988, 108, abstract 43642b.*
J. W. Roddy J. Inorg. Nucl. Chem. 1978, 40, 1787–1791, Oct. 1978.*
F. V. Bright et al, Report, 1988, INDU/DC/GMH/TR–88–17, Feb. 1988.*
G. T. Hefter Solubility Data Ser. 1992, 49, 194–206.*
V. S. Shimdt et al, Chem. Abstr. 1985, 103, 27725x, Jul. 1985.*
C. R. C. Wang et al, J. Phys. Chem. 1987, 91, 3606–3612.*
K. S. Litwiler et al, Anal. Chem. 1991, 63, 797–802, Apr. 1991.*
J. E. Madden et al, Anal. Chim. Acta 1996, 319, 129–134, Jan. 1996.*
O. J. Rolonski et al, J. Fluoresc. 1997, 7, 207S–209S.*
S. Abraham et al, J. Appl. Polym. Sci. 1997, 777–787, Jul. 1997.*
R. Li et al, Anal. Lett. 1997, 30, 1685–1696, Sep. 1997.*
P. Hulthe Analyst , 1970, 95, 351–355.*
T. Tanaka Et Al. Bunseki Kagaku 1978, 27, 247–249.*
T. Tanaka Et Al. Chem. Abstr. 1979, 90, 214582y.*
J. W. Moffett Et Al. Anal. Chim. Acta 1985, 175, 171–179.*
I. Kasahara Et Al. Water Res. 1989, 23, 933–936.*

(List continued on next page.)

Primary Examiner—Arlen Soderquist
(74) Attorney, Agent, or Firm—John J. Karasek; George Kap

(57) ABSTRACT

A method for determining copper (I) concentrations in water or seawater samples. In the method a probe is dipped into the sample for a time sufficient to produce a color change, removed and compared to a color standard to determine the concentration. The probe includes a substrate and an impregnate, bathocuproine, which complexes to copper (I) to produce a colored complex that is not toxic or less toxic to marine organisms than copper (I). The substrate is an ionomeric polymer having hydrophobic chains with hydrophilic cation exchange cites. In a preferred embodiment the substrate is a sulfonated perfluoropolymer.

19 Claims, 2 Drawing Sheets

OTHER PUBLICATIONS

T. Saito *Bunseki Kagaku* 1991, 40, 227–231.*
H. Xue Et Al. *Environ. Sci. Technol.* 1991, 25, 1716–1722.*
T. Saito Et Al. *Talanta* 1994, 41, 811–815.*
D.J.S. Birch Et Al, *Meas. Sci. Technol.* 1995, 6, 243–247.*
R. Glazewski Et Al. *Sci. Total. Environ.* 1996, 189/190, 327–333.*
K. Nara Et Al. *Bunseki Kagaku* 1998, 47, 497–502.*
O.J. Rolinski Et Al. *Meas. Sci. Technol.* 1999, 10, 127–136.*

* cited by examiner

INSOLUBLE IN WATER

2,9-dimethyl-4,7-diphenyl-1,10-phenanthroline

SITU COPPER (I)

BACKGROUND OF THE INVENTION

1. Field of Invention

This invention pertains to in situ determination of copper (I) in an aqueous medium containing copper (I).

2. Description of Prior Art

Ship bottoms, buoys, fishing nets, and other structures submerged in seawater such as cooling water intake or discharge pipes are infested with marine organisms such as barnacles, tube worms and algae that attach to the surface of these structures and cause various problems. It is routine practice to prevent the attachment of these marine fouling organisms by coating the surfaces of the aforementioned items with antifouling paints or coatings.

With the restrictions on the use of toxic coatings in many countries, the boat and ship owners have been using copper oxide-based coatings. The effective life of copper oxide-based coatings on ship or boat hulls rarely exceeds 5 years if the hulls are not mechanically scrubbed or frequently repainted to limit the effect of marine organisms on fuel consumption and speed of the ship or boat so that drag is held to a minimum tolerable quantity. Therefore, a major source of copper in the marine environment is from anti-fouling paints on boat and ship hulls.

The copper-containing antifouling paint on hulls of boats or ships prevents some and reduces other marine organisms from attaching to the hulls. With organism attachment to a hull comes increased drag and thus increased fuel consumption during passage through water. In addition, organism fouling clogs intakes and reduces pipe diameters.

With the requirement to reduce or eliminate environmental contamination, there is a problem with copper (I) levels leached from hulls of boats and ships in port as well as the fines and disposal costs developed during grinding and repainting of the hull.

Furthermore, effectiveness of a copper-containing antifouling paint is tied to leaching of copper (I) ions into the water in which the hull is disposed. When leaching of the copper (I) stops, effectiveness of the paint ceases since leaching of the ionic copper into water is relied upon to kill marine organisms already attached to the hull or to dissuade the marine organisms from settling on the hull. So, in order to determine effectiveness of the paint, boat and ship owners want to know if the paint is leaching copper (I) since copper (I) leaches from a copper-containing antifouling paint.

SUMMARY OF THE INVENTION

It is an object of this invention to determine concentration of copper (I) in water to the level of about 5 ppb.

It is another object of this invention to determine copper (I) concentration by an in situ approach quickly in less than one half hour.

It is another object of this invention to determine copper (I) concentration in seawater by a robust technique which does not require the use of a spectrophotometer or require any special training.

It is another object of this invention to determine if a copper-containing antifouling paint continues to release copper (I) in water.

These and other objects of this invention are attained by a probe which measures concentration of ionic copper (I) by changing color in response to the quantity of ionic copper present in the water. The probe includes a substrate and a BCP compound thereon, the color of which probe is compared to a standard in order to determine concentration of the ionic copper in the water.

DESCRIPTION OF PREFERRED EMBODIMENTS

This invention pertains to an in situ determination of copper (I) concentration in water by a method which includes the steps of dipping a probe into water and comparing the color of the probe to a color standard in order to estimate copper (I) concentration in the water. The probe includes a substrate and an impregnant which changes color in response to concentration of copper (I) in the water, with the color being more intense with increasing copper (I) concentration.

It is known that ionic copper, i.e., copper (I) and copper (II), are biologically beneficial to humans and all life at very low concentrations, however, copper (I) and copper (II) are considered to be toxic to marine organisms at levels above about 10 ppb. With respect to copper (I), it appears that as little as 1 ppb thereof in water is considered to be toxic to marine organisms.

Any substrate can be used herein which can attract both copper (I) and the impregnant which allows the impregnant to react with copper (I) and form a complex that is not toxic to marine organisms or one that is less toxic than copper (I). After trying a number of different substrates, the one that produced desired results was an ionomeric polymer with hydrophobic and hydrophilic regions or components therein based on a perfluorinated polymer. Specifically, Dupont's Nafion® polymers have performed well. Although the Nafion polymers come in liquid and solid forms, the Nafion polymeric film membranes have been found to be preferred. The mostly hydrophobic perflourinated polymer provides chemical and thermal stability similar to Teflon® fluoropolymer resin. Attached to the fluoropolymer chains are perfluorinated cation exchange sites. The polymer is, therefore, permeable to many cations and polar compounds—their size and electrical properties determining their mobility through the polymer and they almost completely reject anions and nonpolar species.

Membranes are typically thin polymer films of less than about 0.01" thick that are usually reinforced with a support cloth made of Teflon polymer. In a typical membrane process, a fluid containing one or more components is in contact with one side of the membrane. The membrane is typically more permeable to one component than the others. The preferred component is transferred through the membrane under the influence of a driving force, such as concentration difference across the membrane, electric potential, or hydrostatic pressure.

Figure 1:
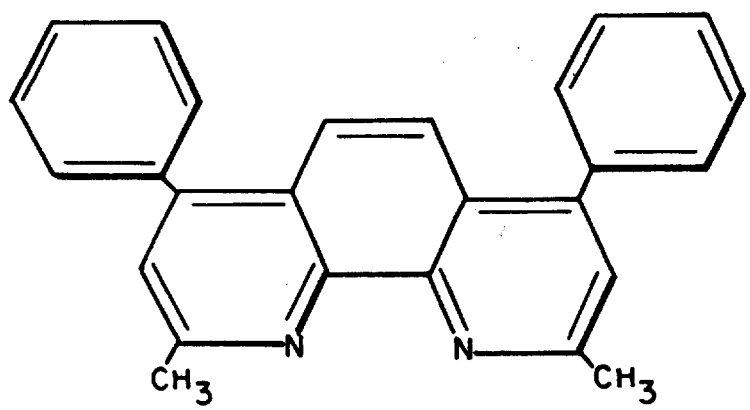
FIG. 1 is a structural formula of the BCP compound or 2,9-dimethyl-4,7-diphenyl-1,10-phenanthroline.

What is needed is a suitable impregnant that attaches to the substrate, is insoluble in an aqueous medium, reacts or complexes with a cuprous ion and produces a color change on reaction or complexation with the cuprous ion, which color progressively intensifies with greater concentration of cuprous ion in the aqueous medium tested for cuprous ion concentration. Although certain derivatives thereof and similar components thereto appear to be useful, the compound that performs admirably herein is bathocuprione (BCP) or 2,9-dimethyl-4,7-diphenyl-1,10 phenanthroline, structural formula of which is given in FIG. 1.

BCP is a highly specific and exceptionally sensitive reagent for the calorimetric determination of copper (I). Just as the introduction of phenyl groups into the 4-and 7-positions of 1,10-phenanthroline greatly increases molar absorptivity of the ferrous derivative, similar substitution into, 2,9-dimethyl-1,10-phenanthroline (neocuprione) greatly increases the intensity of the orange color of the cuprous derivative with the result that the molar absorptivity of the cuprous derivative in water is 14, 160 L/Mcm in contrast to that of 7,950 L/Mcm of the cuprous derivative of neocuprione.

It should be apparent that other impregnants can be used in place of BCP. Preferred, however, are impregnants which produce a vivid color change on reaction with copper (I). Molar absorptivity of the cuprous derivative of BCP varies somewhat with the fluid it is in 13,900 L/Mcm in water; 14,160 L/Mcm in n-hexyl alcohol; and 14,200 L/Mcm in isoamyl alcohol.

Sufficient impregnant should be disposed on the substrate to react with copper (I). The BCP impregnant is loaded into substrate at about 1 mg of BCP per gram of the Nafion film. The BCP reacts in a 2:1 molar ratio with copper (I). When BCP comes in contact with copper (I), it is believed that copper (I) bonds between the nitrogen atoms of BCP and creates an orange color on formation of the cuprous derivative thereof, or the BCP chelate ring compound, i.e., a complex. BCP complexes copper (I) due to the unique property to form organometallic bonds and develops orange color over the pH range of 3.5–11, preferably 7–9, when temperature of the aqueous medium is 0–100° C., preferably 0–40° C., and especially 20–25° C. at atmospheric conditions.

EXAMPLES

Using Nafion 117/112 self-supporting membrane film 0.007"/0.002" thick as the substrate and BCP as the impregnant, procedure to make a test strip was as follows: the film substrate was cut into strips, typically rectangular measuring 2"×1". The strips were placed in 1M nitric acid and boiled for 1 hour to eliminate impurities. After boiling in nitric acid, the strips were removed and rinsed with deionized water and then stored in deionized water overnight or about 12 hours to leach out any remaining nitric acid.

A 0.001 M solution of BCP was prepared in 100% ethanol and the BCP solution was filled into small transparent screw cap vials measuring about 2" in height and ½" in diameter. This was followed by immersion of the previously boiled strips in the BCP solution in each vial and storage for 24 hours to allow diffusion of the the BCP molecules into the strips. The strips were then removed from the vials and immersed in the standard solution for 6–24 hours until the strips turned orange.

The 100-ml deionized water standard solution contained 1000 ppb copper (I) and had the following composition initially:

(a) 1000 ppb copper (II)
(b) 2 ml 50% hydrochloric acid
(c) 10 ml hydroxylamine hydrochloride
(d) 10 ml sodium acetate In the standard solution, the 2 ml of hydrochloric acid and the 10 ml of hydroxylamine hydrochloride function to convert copper (II) to copper (I)and the 10 ml of sodium acetate functions as a buffer to stabilize the solution at pH of 5.5. The strips were then removed from the standard solution, rinsed in deionized water and de-colored by placing the strips n 1 M nitric acid for 1 hour, following which the strips were removed and immersed in deionized water. At this point, the strips were colorless. The de-colored strips were stored in deionized water until use.

To regenerate the strips after use, the used strips of an orange color varying in intensity from faint orange to vivid orange, can be placed in 1M nitric acid and held there until the orange color fades to colorless. Then, the strips can be rinsed in deionized water and stored in fresh deionized water until re-use.

Figure 2:
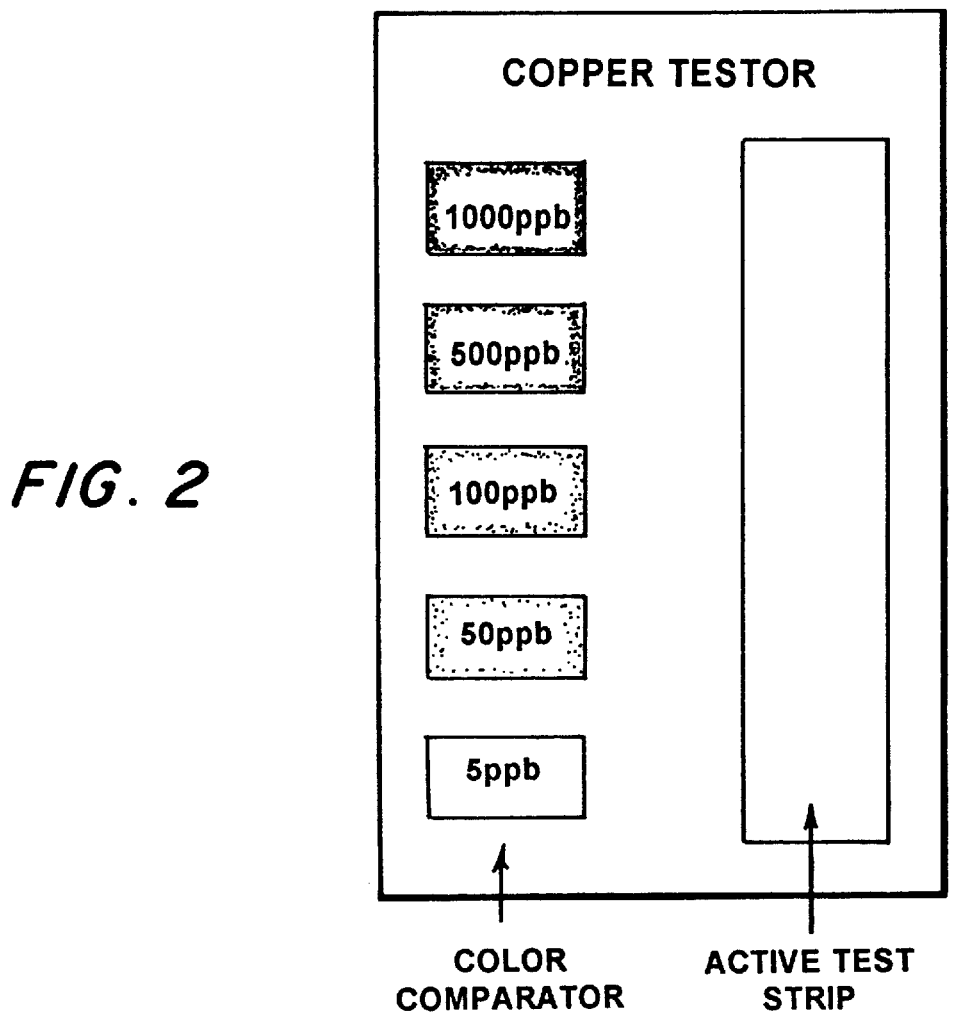
FIG. 2 shows the color comparator standard and the active strip composed of an ionomeric film substrate impregnated with bathocuproine (BCP) which is used in the determination of copper (I) concentration.
Figure 3:
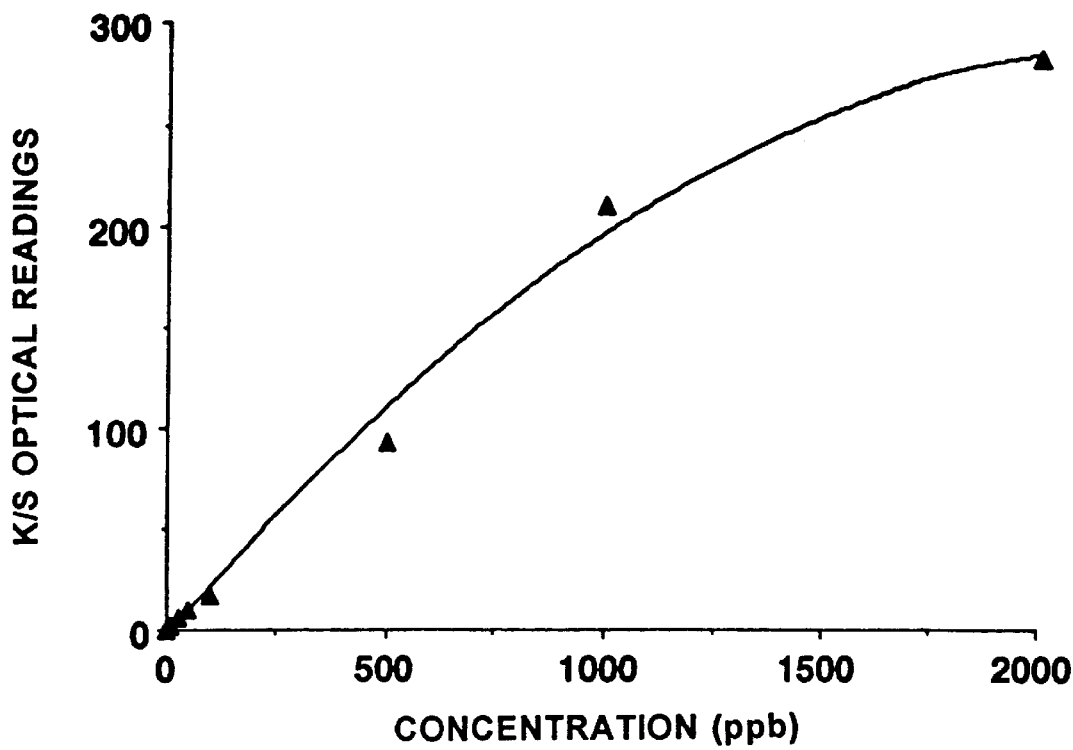
FIG. 3 illustrates the response of the ionomeric film substrate impregnated with bathocuproine to copper (I) in seawater.
Figure 4:
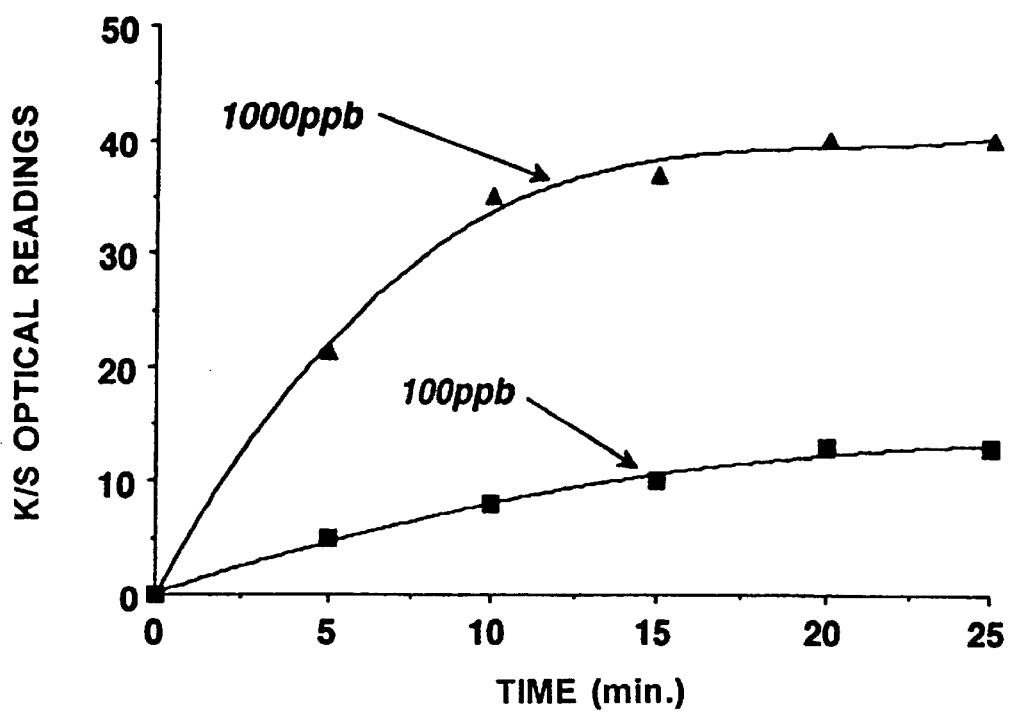
FIG. 4 Illustrates the response of BCP in the substrate polymer film to different concentrations of copper (I) in seawater.

To test for copper (I) concentration of an aqueous sample, an active strip or probe was placed in the water and kept in the water for 20 minutes during which time, the active strip turned orange to indicate presence of copper (I). Intensity of the orange strip was compared to a standard which indicated concentration of copper (I) in the aqueous sample in parts per billion (ppb) of copper (I), where ppb=$\mu$g/l. FIG. 2 illustrates that active strip or probe and the color compactor consisting of 5 rectangular spaces of varying orange intensity corresponding to copper (I) concentration from 5 ppb to 1000 ppb. At 2000 ppb of copper (I) in the sample, the orange color is so intense that dilution is necessary to obtain accurate readings.

A spectrophotometer can be used to measure concentration of copper (I) at 484 nm and concentration of copper (II) at 750 nm. A probe of a Nafion film impregnated with BCP indicates presence of copper (I) when this probe is colored orange. A test strip of Nafion film impregnated with a BCP solution, will show presence of copper (II) when the test strip is believed to be colored differently. If the presence of copper (II) is suspected in the aqueous sample, copper (II) can be reduced to copper (I) with a reducing agent, such as hydroxylamine hydrochloride, and then the aqueous sample can be tested for copper (I) concentration. In this manner, concentration of total copper, i.e., copper (I) and copper (II) can be determined. Also, since copper (I) in water oxidizes to copper (II) in about 4 hours or longer, it may be desirable to determine concentration of both forms of ionic copper since both forms are considered to be toxic to marine organisms.

A copper-containing antifouling paint coated on a substrate and immersed in a typical port seawater having 35.2 ppt salinity, pH of 7.8, and a temperature of 25° C., leaches copper (I) at a slow rate and then it is assumed that it reaches a plateau which continues for up to 5 years.

Copper (I) released into different types of water varies greatly. New copper-containing antifouling paint that has not been immersed in seawater shows slow copper (I) release over time with minimal releases in non-seawater. Leaching of copper (I) begins within the first 15 minutes of immersing the paint in seawater, within 5 hours in pond water and within 165 hours in distilled water. This indicates that the antifouling paint should have seawater to trigger quick copper (I) release.

As used herein, copper (I) is cuprous ion which is also designated as $Cu^{+1}$.

While presently preferred embodiments have been shown of the novel in situ method for determining concentration of copper (I) in water, and of the several modifications discussed, persons skilled in this art will readily appreciate that various additional changes and modifications may be made without departing from the spirit of the invention as defined and differentiated by the claims that follow.

What is claimed is:

1. A non-spectroscopic method for determining copper (I) concentration in water down to a level of 5 ppb comprising the steps of:
   (a) contacting a probe with water for a duration sufficient to develop color in the probe,
   (b) removing the probe from contact with the water, and
   (c) comparing color of the probe with a color standard correlated to copper (I) concentration in the water, the probe comprising an ionomeric polymer substrate having hydrophobic chains with hydrophilic cation exchange cites attached thereto and an impregnant capable of reacting with copper (I) to form a complex with copper (I) that is not toxic or less toxic than copper (I) to marine organisms.

2. The method of claim 1 wherein the water is selected from the group consisting of seawater, pond water, distilled water, and mixtures thereof; and wherein the substrate is a perfluorinated polymer film.

3. The method of claim 2 wherein the water is seawater and the complex is non-toxic to marine organisms.

4. The method of claim 3 wherein temperature of the water is 0–100° C. and pH of the water is 3.5–11.

5. The method of claim 3 wherein the probe is a calorimetric test strip and wherein temperature of the water is 0–40° C. and pH of the water is 3.5–11.

6. The method of claim 5 wherein the the substrate is a perfluorinated cation polymer film; and wherein the impregnant is insoluble in the water and forms a complex with copper (I).

7. The method of claim 6 wherein the substrate is a sulfonated and perfluorinated polymer film and the impregnant is a reagent for calorimetric determination of copper.

8. The method of claim 7 wherein the impregnant is bathocuproine; wherein temperature of the it water is 20–25° C. and pH of the water is 7–9; wherein the concentration of the impregnant in the substrate is about 1 microgram per gram of the substrate; and wherein amount of the impregnant reacting with copper (I) is in a molar ratio of 2/1.

9. The method of claim 7 including the step of reducing copper (II) in the water to copper (I).

10. The method of claim 9 including the steps of boiling the non-impregnated substrate in nitric acid and diffusing the impregnant into the substrate.

11. The method of claim 10 wherein the color standard comprises multiple strips on the standard of varying orange color intensity, with the more intense orange colored strips indicating a higher concentration of copper (I) in the water.

12. A method for determining copper (I) concentration down to a level of 5 ppb in seawater containing copper (I) leached from a copper-containing antifouling paint disposed on a surface as a coating, comprising the steps of:
   (a) dipping a probe into the seawater for a duration sufficient to develop orange color in the probe,
   (b) removing the probe from the seawater, and
   (c) comparing color of the probe with a color standard correlated to copper (I) concentration in the seawater, the probe is in the form of a strip comprising an ionomeric polymer substrate having hydrophobic chains with hydrophylic cation exchange sites attached thereto and an impregnant diffused throughout the substrate, the impregnant capable of complexing with copper (I) to form a non-toxic complex.

13. The method of claim 12 wherein the substrate is a perfluorinated polymer film.

14. The method of claim 12 wherein temperature of the seawater is 0–100° C., pH of the water is 3.5–11, and salinity of the water is about 35.2 ppt.

15. The method of claim 14 wherein temperature of the seawater is 0–40° C.

16. The method of claim 15 wherein the substrate is perfluorinated cation polymer film; and wherein the impregnant is insoluble in seawater and can form a complex with copper (1).

17. The method of claim 16 wherein the substrate is a sulfonated and perfluorinated polymer and the impregnant is a for calorimetric determination of copper.

18. The method of claim 17 including the steps of reducing copper (II) in the water to copper (I), boiling the non-impregnated substrate in nitric acid, and diffusing the impregnant into the substrate.

19. The method of claim 18 wherein the impregnant is bathocuproine; wherein temperature of the water is 20–25° C. and pH of the water is 7–9; wherein amount of the impregnant is about 1 microgram per gram of the substrate; wherein amount of the impregnant reacting with amount of the copper (I) on a molar basis is in the ratio of 2/1; and wherein the color standard comprises multiple strips on the substrate of varying orange color intensity, with the more intense orange colored strips indicating a higher concentration of copper (I) in the water.

* * * * *